US00PP29853P2

(12) United States Plant Patent
Kolster

(10) Patent No.: US PP29,853 P2
(45) Date of Patent: Nov. 20, 2018

(54) ***HYDRANGEA* PLANT NAMED 'KOLMAKILIMA'**

(50) Latin Name: *Hydrangea paniculata*
Varietal Denomination: KOLMAKILIMA

(71) Applicant: Peter Rudolf Kolster, Boskoop (NL)

(72) Inventor: Peter Rudolf Kolster, Boskoop (NL)

(73) Assignee: KOLSTER HOLDING, BV, Boskoop (NL)

( * ) Notice: Subject to any disclaimer, the term of this patent is extended or adjusted under 35 U.S.C. 154(b) by 12 days.

(21) Appl. No.: 15/530,969

(22) Filed: Mar. 30, 2017

(51) Int. Cl.
*A01H 5/02* (2018.01)

(52) U.S. Cl.
USPC ..... Plt./250

(58) Field of Classification Search
USPC ..... Plt./250
See application file for complete search history.

*Primary Examiner* — Anne Marie Grunberg
(74) *Attorney, Agent, or Firm* — Penny J. Aguirre

(57) ABSTRACT

A new cultivar of *Hydrangea paniculata* plant named 'KOLMAKILIMA' that is characterized by its short and strong stems, and its mophead-like, long, conical shaped inflorescences.

2 Drawing Sheets

Botanical classification: *Hydrangea paniculata.*
Varietal denomination: 'KOLMAKILIMA'.

CROSS REFERENCE TO RELATED APPLICATIONS

This application is related to a European plant breeders' rights application filed Dec. 18, 2014, application no. 2014/3471 and a Canadian plant breeders' rights application filed on Apr. 10, 2015, application No. 15-8595. There have been no offers for sale anywhere in the world prior to the effective filing of this Application. No accessibility to one of ordinary skill in the art could have been derived from the printed plant breeders' rights documents.

BACKGROUND OF THE INVENTION

The present invention relates to a new and distinct cultivar of *Hydrangea paniculata* and will be referred to hereafter by its cultivar name, 'KOLMAKILIMA'. 'KOLMAKILIMA' represents a new smooth *hydrangea*, a perennial shrub grown for landscape use.

'KOLMAKILIMA' arose from an ongoing breeding program by the Inventor in Boskoop, The Netherlands. The objective of the breeding program was to obtain new cultivars of *Hydrangea paniculata* with short, strong stems and mophead-like blooms. 'KOLMAKILIMA' arose as a seedling derived from open pollination of *Hydrangea paniculata* 'Kolmagimo' U.S. Plant Pat. No. 18,438 in July of 2006. 'KOLMAKILIMA' was selected a single unique plant from amongst the resulting seedlings in July of 2010.

Asexual propagation of the new cultivar was first accomplished by stem cuttings by the Inventor in Boskoop, The Netherlands in 2009. Asexual propagation by stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'KOLMAKILIMA' as a unique cultivar of *Hydrangea paniculata.*

1. 'KOLMAKILIMA' exhibits short and strong stems.
2. 'KOLMAKILIMA' exhibits mophead-like, long, conical shaped inflorescences.

The female parent of 'KOLMAKILIMA', 'Kolmagimo' differs from 'KOLMAKILIMA' in having a longer stems and in having smaller inflorescences. 'KOLMAKILIMA' can be most closely compared to *Hydrangea paniculata* cultivars 'Kolmamon' (not patented), 'Bokraflame' (U.S. Plant Pat. No. 22,111) and 'Kolmavesu' (U.S. Plant Pat. No. 26,928). 'Kolmamon' differs from 'KOLMAKILIMA' in having inflorescences that are shorter and less elongated in shape. 'Bokraflame' differs from 'KOLMAKILIMA' in having inflorescences that are shorter and that turn pink earlier. 'Kolmavesu' differs from 'KOLMAKILIMA' in having inflorescences with less showy sterile flowers.

BRIEF DESCRIPTION OF THE DRAWINGS

The accompanying colored photographs illustrate the overall appearance and distinct characteristics of the new *Hydrangea*. The photographs were taken of a plant two years in age as grown outdoors in a trial plot in Boskoop, The Netherlands.

The photograph in FIG. 1 provides a view of the plant habit of 'KOLMAKILIMA' in bloom.

Figure 1:
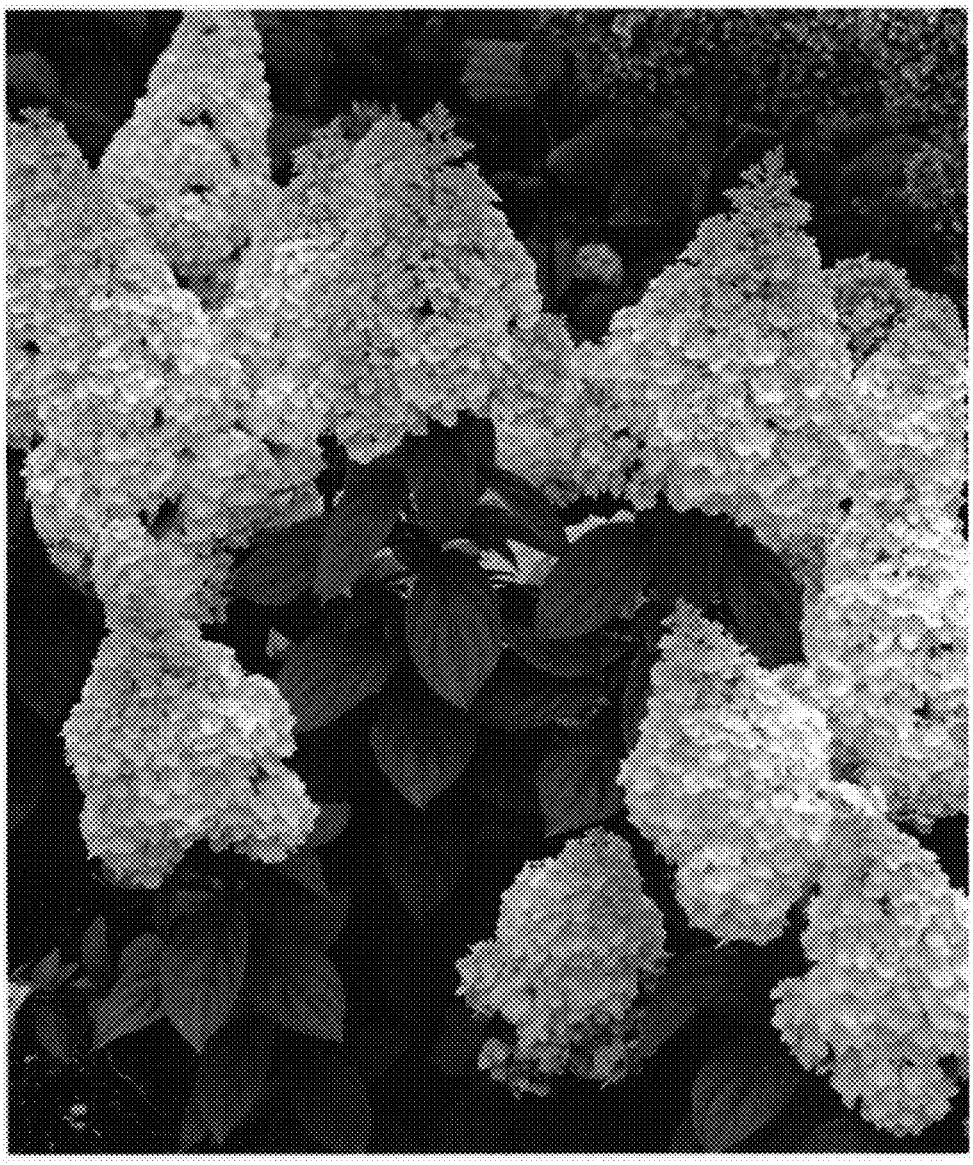
Figure 2:
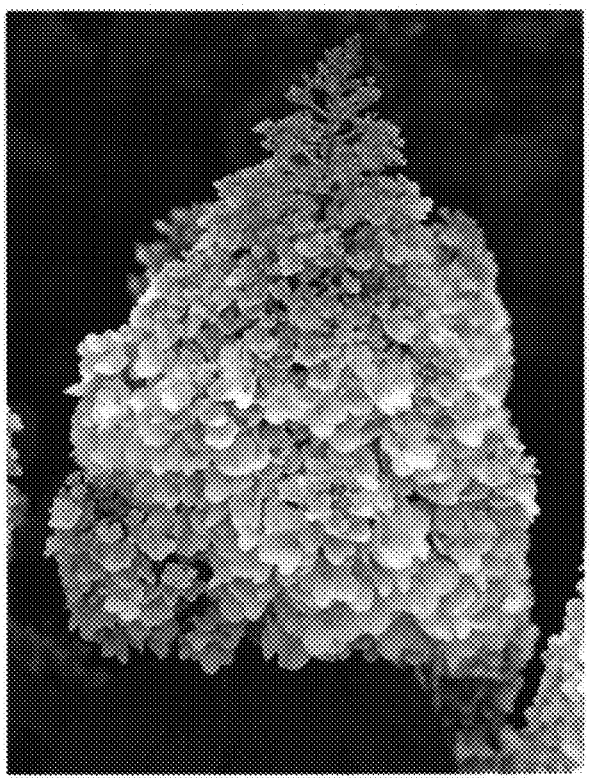

The photograph in FIG. 2 provides a close-up view of an inflorescence of 'KOLMAKILIMA'.

Figure 3:
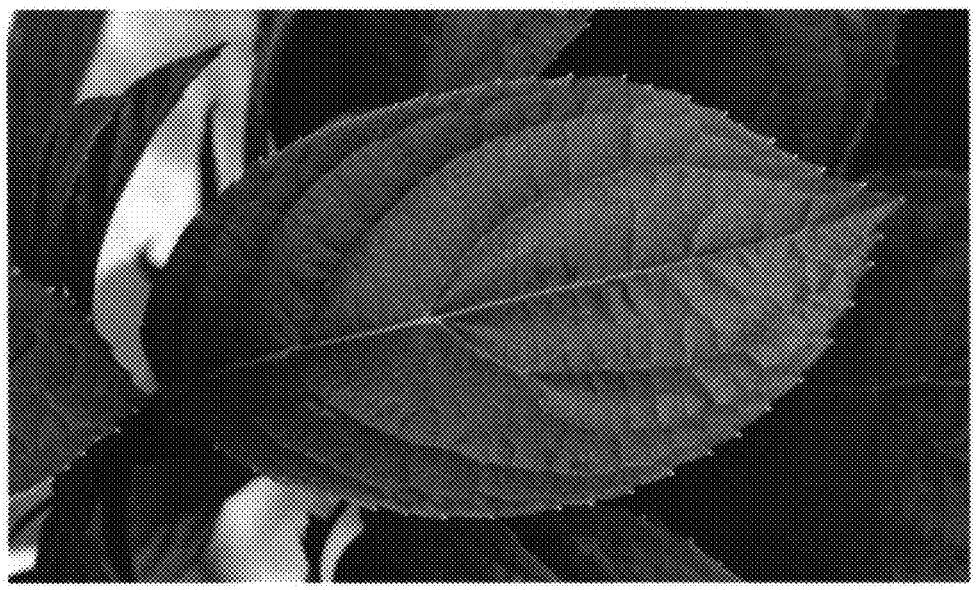

The photograph in FIG. 3 provides a close-up view of the leaf of 'KOLMAKILIMA'.

The colors in the photographs are as close as possible with the photographic and printing technology utilized and the color values cited in the detailed botanical description accurately describe the colors of the new *Hydrangea.*

BOTANICAL DESCRIPTION OF THE PLANT

The following is a detailed description of plants two years in age as grown outdoors in a trial plot in Boskoop, The Netherlands. The phenotype of the new cultivar may vary with variations in environmental, climatic, and cultural conditions, as it has not been tested under all possible environmental conditions. The color determination is in accordance with The 2015 R.H.S. Colour Chart of The Royal Horticultural Society, London, England, except where general color terms of ordinary dictionary significance are used.

General description:

*Blooming period*.—From July to September in The Netherlands.

*Plant type*.—Perennial shrub, mophead-like panicles.

*Plant habit*.—Upright with sturdy stems.

*Height and spread*.—An average of 1.2 m in height and 80 cm in spread for a 2 year-old plant in the landscape.

*Hardiness*.—At least in U.S.D.A. Zones 5 to 10.

*Diseases and pests*.—No susceptibility and resistance to pests and diseases has been observed.

*Root description*.—Fibrous and fine.

*Propagation*.—Stem cuttings.

*Time required for root development*.—An average of 3.5 weeks for root initiation with a small finished plant produced in about 12 months.

*Growth rate*.—Moderate.

Stem description:

*Stem shape*.—Rounded.

*Stem color*.—New growth; 183D, mature wood; 199A, 199B and 199C, older bark; 200D.

*Stem size*.—Average of 52.7 cm in length (excluding inflorescence) and 8.5 mm in diameter.

*Stem surface*.—Glabrous.

*Stem aspect*.—Average angle 65° (soil level=0°).

*Internode length*.—Average of 6.8 cm.

*Branching*.—Average of 10 basal branches.

Foliage description:

*Leaf shape*.—Ovate.

*Leaf division*.—Simple.

*Leaf size*.—Average of 11.3 cm in length and 7 cm in width.

*Leaf base*.—Obtuse.

*Leaf apex*.—Apiculate.

*Leaf venation*.—Pinnate, color upper surface; 147B, fading to 148B to 148A towards the leaf base, color lower surface; 145C.

*Leaf margins*.—Serrate.

*Leaf attachment*.—Petiolate.

*Leaf arrangement*.—Opposite.

*Leaf surface*.—Upper surface smooth and slightly rugose, lower surface rugose and covered with hairs on the main and secondary veins, 0.5 mm in length and 157D in color.

*Leaf color*.—Immature leaves upper surface; 143A and 144A, immature leaves lower surface; 146B, mature leaves upper surface; NN137B, mature leaves lower surface; 146B and 147B.

*Petioles*.—Average of 1.6 cm in length and 3 mm in diameter, upper surface; smooth and matte, 148A, margined 176A in color, lower surface; smooth, slightly glossy and 149B in color.

Inflorescence description:

*Inflorescence type*.—Terminal panicle.

*Lastingness of inflorescence*.—An average of one week.

*Inflorescence number*.—One per lateral or sublateral stem.

*Inflorescence size*.—Average of 36.2 cm in depth and 20.5 cm in diameter.

*Flower number*.—Average of 1,000 sterile flowers and 420 fertile flowers per panicle.

*Flower fragrance*.—No fragrance.

*Flower aspect*.—Sterile flowers; upright to outward and slightly drooping, more drooping when fading, fertile flowers; upright.

*Flower size*.—Sterile flowers; an average of 2.4 cm in diameter and 9 mm in depth, fertile flowers; an average of 8 mm in diameter and 4.5 mm in depth.

*Flower type*.—Rotate.

*Flower buds*.—Sterile flowers; average of 4 mm in length and diameter, obovate in shape, 150C in color, fertile flowers; average of 2 mm in length and diameter, obovate in shape, 157B in color.

*Peduncles*.—Strong, an average of 10 cm in length and 4 mm in width, a blend of 144B and 183D in color, surface glabrous.

*Pedicels*.—Sterile flowers; held at a 45° angle from vertical, an average of 1.4 cm in length and 1 mm in width, moderate strength, 150D in color, dull, moderately pubescent surface covered with adpressed hairs; 0.3 mm in length and too small to measure color, fertile flowers; held at an average of 15°, an average of 6 mm in length and 1 mm in diameter, moderate strength, 155C in color, surface is matte and moderately to densely covered with thin pubescence; an average of 0.2 mm in length and too small to measure color.

*Petals*.—Sterile flowers; average of 4 to 5, rotate in arrangement, ovate to concave in shape, entire margin, acute apex, cuneate base, average of 2 mm in length and 1 mm in width, upper and lower surface glabrous and matte, color; upper and lower surface NN155D, fertile flowers; average of 4 to 5, rotate in arrangement, ovate and concave in shape, an average of 2 cm in length and 1 cm width, acute apex, cuneate base, entire margins, upper and lower surface glabrous and matte, color; when opening upper and lower surface NN155D, upper and lower surface when fully open; dropped when maturing.

*Sepals*.—Sterile flowers; average of 4, rotate in arrangement, ovate to broad ovate in shape, occasionally obovate in shape, an average of 1.2 cm in length and 9 mm width, obtuse apex, cuneate base, entire margins, matte and glabrous on upper and lower surface, color: upper surface when opening and fully open 155A, fading to 145A, lower surface when opening and fully open 155B, fading to 145C, fertile flowers; average of 5, rotate in arrangement, near triangular in shape, acuminate apex, broad cuneate base, entire margins, an average of 1 mm in length and width, both surfaces glabrous and matte, color; upper and lower surface when opening and fully open 157D.

Reproductive organs: (fertile flowers perfect, sterile flowers staminate).

*Stamens*.—Sterile flowers; average of 8, filament is 1.5 mm in length and NN155C in color, anther is oblong in shape, 0.05 mm in length and 155A in color, pollen is moderate in quantity and 160D in color, fertile flowers; average of 10, filament is 4 mm in length and NN155C in color, anther is oblong, 0.5 mm in length and 155A in color, pollen amount is moderate and 160D in color.

*Pistils*.—Sterile flowers; no gynoecium present in sterile flowers, fertile flowers; average of 2, occasionally 3, an average of 1 mm in length, stigma is club-shaped and NN155D in color, style is an average of 0.5 mm in length and NN155B in color, ovary is 157A in color.

*Fruit and seed*.—No fruit or seed production has been observed.

It is claimed:

1. A new and distinct cultivar of *Hydrangea* plant named 'KOLMAKILIMA' substantially as herein illustrated and described.

* * * * *